US012703764B2

(12) United States Patent
Smith

(10) Patent No.: US 12,703,764 B2
(45) Date of Patent: Aug. 11, 2026

(54) HUMAN IgE MONOCLONAL ANTIBODIES TO ANTIBODIES TO ALPHA-GAL (GALACTOSE-α-1,3-GALACTOSE) AND USES THEREFOR

(71) Applicant: VANDERBILT UNIVERSITY, Nashville, TN (US)

(72) Inventor: Scott A. Smith, White Bluff, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 578 days.

(21) Appl. No.: 18/256,917

(22) PCT Filed: Dec. 13, 2021

(86) PCT No.: PCT/US2021/063107

§ 371 (c)(1),
(2) Date: Jun. 9, 2023

(87) PCT Pub. No.: WO2022/132641

PCT Pub. Date: Jun. 23, 2022

(65) Prior Publication Data

US 2024/0026035 A1 Jan. 25, 2024

Related U.S. Application Data

(60) Provisional application No. 63/125,099, filed on Dec. 14, 2020.

(51) Int. Cl.

| | |
|---|---|
| ***C07K 16/44*** | (2006.01) |
| ***A61K 39/00*** | (2006.01) |
| ***A61K 39/35*** | (2006.01) |
| ***A61P 37/08*** | (2006.01) |
| ***G01N 33/53*** | (2006.01) |
| ***G01N 33/68*** | (2006.01) |

(52) U.S. Cl.

CPC .............. *C07K 16/44* (2013.01); *A61K 39/00* (2013.01); *A61K 39/35* (2013.01); *A61P 37/08* (2018.01); *G01N 33/5308* (2013.01); *G01N 33/6854* (2013.01); *A61K 2039/577* (2013.01); *C07K 2317/41* (2013.01); *C07K 2317/52* (2013.01); *C07K 2317/72* (2013.01); *C07K 2317/92* (2013.01); *C07K 2317/94* (2013.01); *G01N 2400/00* (2013.01); *G01N 2800/24* (2013.01)

(58) Field of Classification Search

CPC . A61P 37/08; G01N 33/6854; G01N 2800/24
See application file for complete search history.

(56) References Cited

U.S. PATENT DOCUMENTS

| | | | |
|---|---|---|---|
| 2003/0228637 | A1 | 12/2003 | Wang |
| 2011/0124013 | A1 | 5/2011 | Banik et al. |
| 2012/0219975 | A1 | 8/2012 | Banik et al. |
| 2017/0283501 | A1 | 10/2017 | Swanson et al. |
| 2018/0244802 | A1 | 8/2018 | Pruess |
| 2020/0115439 | A1 | 4/2020 | Smith |

FOREIGN PATENT DOCUMENTS

| | | |
|---|---|---|
| CN | 108872584 A | 11/2018 |
| WO | WO 2020/077144 | 4/2020 |

OTHER PUBLICATIONS

European Search Report issued in European Application No. 21907563.7, dated Oct. 22, 2024.
International Preliminary Report on Patentability issued in International Application No. PCT/US2021/063107, dated Jun. 29, 2023.
International Search Report and Written Opinion issued in International Application No. PCT/US2021/063107, dated May 4, 2022.
Invitation to Pay Additional Fees issued in International Application No. PCT/US2021/063107, dated Feb. 25, 2022.

*Primary Examiner* — Gary B Nickol
*Assistant Examiner* — Bryan William Heck
(74) *Attorney, Agent, or Firm* — pH IP Law

(57) ABSTRACT

The present disclosure is directed to human IgE antibodies and fragments thereof binding to galactose-α-1, 3-galactose, a known red meat allergen, and methods for use thereof.

23 Claims, 4 Drawing Sheets

Specification includes a Sequence Listing.

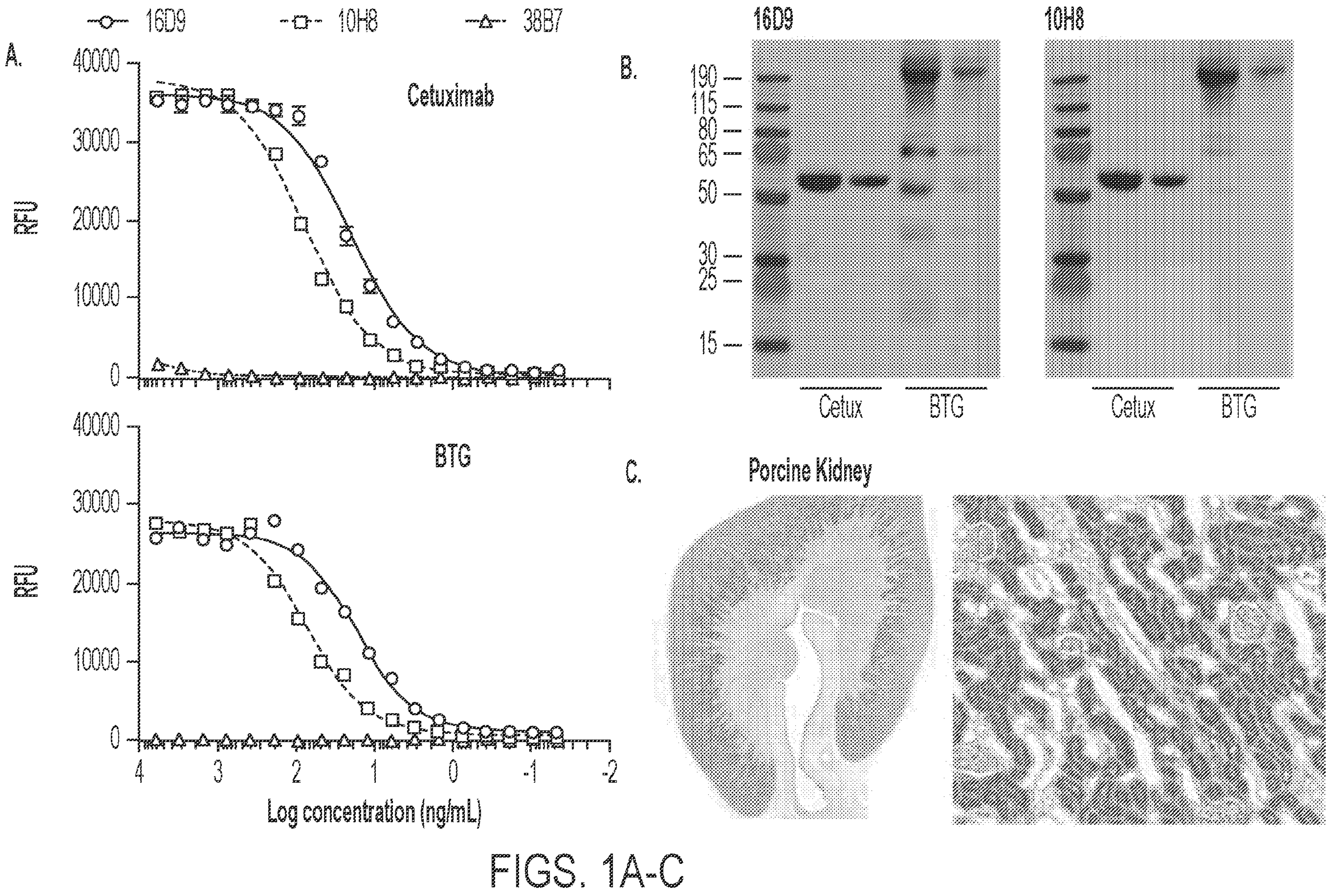
FIGS. 1A-C

A.

Cetuximab EC50 15 min

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|---|
| | A | 0.30 | 0.33 | 0.26 | 0.44 | 0.32 | 0.24 | 0.23 | 0.33 | 0.33 | 0.33 | 0.23 | 0.30 | 0.23 | 0.37 | 0.31 | 0.26 | 0.26 | 0.28 | 0.20 | 0.23 | 0.22 | 0.20 | 0.20 | 0.26 |
| 16D9 | B | 3.26 | 3.20 | 3.16 | 3.27 | 3.32 | 3.28 | 3.01 | 3.11 | 3.08 | 2.66 | 1.93 | 1.42 | 0.89 | 0.73 | 0.64 | 0.38 | 0.36 | 0.29 | 0.35 | 0.28 | 0.25 | 0.32 | 0.28 | 0.27 |
| 16D9 | C | 3.27 | 3.29 | 3.30 | 3.35 | 3.32 | 3.32 | 3.06 | 3.28 | 3.08 | 2.74 | 1.97 | 1.36 | 0.78 | 0.64 | 0.71 | 0.51 | 0.32 | 0.30 | 0.23 | 0.24 | 0.24 | 0.35 | 0.26 | 0.27 |
| 16D9 | D | 3.28 | 3.28 | 3.15 | 3.28 | 3.30 | 3.29 | 3.14 | 3.20 | 3.00 | 2.60 | 1.94 | 1.26 | 0.80 | 0.62 | 0.55 | 0.37 | 0.30 | 0.29 | 0.27 | 0.33 | 0.28 | 0.25 | 0.29 | 0.27 |
| — | E | 0.21 | 0.21 | 0.15 | 0.19 | 0.16 | 0.19 | 0.14 | 0.19 | 0.14 | 0.19 | 0.15 | 0.21 | 0.15 | 0.18 | 0.15 | 0.22 | 0.14 | 0.23 | 0.20 | 0.22 | 0.14 | 0.27 | 0.19 | 0.31 |
| — | F | 0.21 | 0.22 | 0.23 | 0.23 | 0.16 | 0.24 | 0.16 | 0.22 | 0.14 | 0.21 | 0.17 | 0.24 | 0.15 | 0.20 | 0.16 | 0.21 | 0.14 | 0.21 | 0.15 | 0.21 | 0.15 | 0.23 | 0.18 | 0.24 |
| 10H8 | G | 3.28 | 3.22 | 3.24 | 3.17 | 3.08 | 2.86 | 2.42 | 1.77 | 1.07 | 0.67 | 0.43 | 0.36 | 0.23 | 0.26 | 0.21 | 0.25 | 0.17 | 0.23 | 0.16 | 0.24 | 0.17 | 0.22 | 0.20 | 0.35 |
| 10H8 | H | 3.25 | 3.21 | 3.22 | 3.18 | 3.08 | 2.89 | 2.47 | 1.78 | 1.13 | 0.72 | 0.45 | 0.37 | 0.23 | 0.26 | 0.23 | 0.25 | 0.21 | 0.26 | 0.18 | 0.27 | 0.16 | 0.26 | 0.18 | 0.23 |
| 10H8 | I | 3.28 | 3.22 | 3.22 | 3.17 | 3.08 | 2.91 | 2.47 | 1.76 | 1.10 | 0.71 | 0.48 | 0.36 | 0.23 | 0.25 | 0.17 | 0.23 | 0.17 | 0.22 | 0.16 | 0.22 | 0.18 | 0.24 | 0.20 | 0.24 |
| — | J | 0.14 | 0.18 | 0.22 | 0.19 | 0.15 | 0.18 | 0.14 | 0.16 | 0.14 | 0.18 | 0.13 | 0.17 | 0.13 | 0.16 | 0.18 | 0.19 | 0.14 | 0.17 | 0.15 | 0.18 | 0.14 | 0.22 | 0.14 | 0.19 |
| — | K | 0.14 | 0.18 | 0.14 | 0.17 | 0.14 | 0.17 | 0.13 | 0.19 | 0.13 | 0.17 | 0.13 | 0.16 | 0.13 | 0.17 | 0.13 | 0.17 | 0.14 | 0.17 | 0.15 | 0.17 | 0.15 | 0.17 | 0.18 | 0.20 |
| M86 | L | 3.17 | 3.06 | 2.81 | 2.12 | 1.34 | 0.78 | 0.49 | 0.31 | 0.27 | 0.20 | 0.18 | 0.16 | 0.13 | 0.17 | 0.15 | 0.16 | 0.14 | 0.17 | 0.14 | 0.17 | 0.14 | 0.17 | 0.14 | 0.19 |
| M86 | M | 3.17 | 3.04 | 2.77 | 2.40 | 1.30 | 0.73 | 0.47 | 0.29 | 0.21 | 0.18 | 0.15 | 0.15 | 0.14 | 0.16 | 0.14 | 0.15 | 0.14 | 0.15 | 0.14 | 0.17 | 0.14 | 0.17 | 0.29 | 0.21 |
| M86 | N | 3.20 | 3.07 | 2.83 | 2.05 | 1.05 | 0.53 | 0.47 | 0.29 | 0.19 | 0.19 | 0.15 | 0.16 | 0.14 | 0.16 | 0.13 | 0.14 | 0.14 | 0.14 | 0.15 | 0.15 | 0.14 | 0.15 | 0.18 | 0.20 |
| | O | 0.16 | 0.15 | 0.16 | 0.15 | 0.16 | 0.16 | 0.16 | 0.16 | 0.17 | 0.15 | 0.14 | 0.15 | 0.14 | 0.16 | 0.14 | 0.15 | 0.15 | 0.21 | 0.16 | 0.15 | 0.17 | 0.18 | 0.16 | 0.22 |
| | P | 0.19 | 0.17 | 0.17 | 0.16 | 0.23 | 0.17 | 0.18 | 0.17 | 0.28 | 0.17 | 0.16 | 0.15 | 0.19 | 0.22 | 0.15 | 0.17 | 0.21 | 0.18 | 0.17 | 0.21 | 0.26 | 0.41 | 0.21 | 0.19 |

Halving dilutions, 10 μg/mL start

BTG EC50 15 min

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | Approx. $EC_{50}$ |
|---|---|---|---|---|---|---|---|---|---|---|---|---|---|---|---|---|---|---|---|---|---|---|---|---|---|
| A | 0.34 | 0.41 | 0.31 | 0.40 | 0.38 | 0.51 | 0.35 | 0.43 | 0.40 | 0.37 | 0.40 | 0.39 | 0.38 | 0.36 | 0.36 | 0.34 | 0.33 | 0.32 | 0.33 | 0.33 | 0.33 | 0.33 | 0.32 | 0.31 | |
| B | 3.22 | 3.24 | 3.23 | 3.23 | 3.19 | 3.22 | 3.25 | 3.20 | 3.09 | 2.90 | 2.66 | 2.00 | 1.41 | 1.12 | 1.01 | 0.68 | 0.54 | 0.42 | 0.45 | 0.39 | 0.41 | 0.44 | 0.43 | 0.40 | 8 ng/mL |
| C | 3.24 | 3.24 | 3.23 | 3.21 | 3.26 | 3.12 | 1.23 | 3.16 | 3.12 | 2.99 | 2.62 | 1.88 | 1.25 | 1.04 | 0.90 | 0.67 | 0.46 | 0.42 | 0.38 | 0.39 | 0.39 | 0.35 | 0.36 | 0.35 | |
| D | 3.23 | 3.24 | 3.21 | 3.18 | 3.25 | 3.25 | 3.24 | 3.16 | 3.09 | 2.87 | 2.61 | 1.94 | 1.47 | 1.08 | 0.89 | 0.60 | 0.49 | 0.45 | 0.38 | 0.44 | 0.44 | 0.35 | 0.49 | 0.37 | |
| E | 0.32 | 0.34 | 0.25 | 0.32 | 0.25 | 0.31 | 0.27 | 0.29 | 0.26 | 0.30 | 0.34 | 0.32 | 0.28 | 0.32 | 0.27 | 0.30 | 0.28 | 0.32 | 0.27 | 0.33 | 0.26 | 0.33 | 0.32 | 0.34 | |
| F | 0.30 | 0.32 | 0.27 | 0.32 | 0.25 | 0.31 | 0.27 | 0.33 | 0.24 | 0.33 | 0.26 | 0.33 | 0.25 | 0.33 | 0.27 | 0.36 | 0.27 | 0.34 | 0.33 | 0.34 | 0.28 | 0.36 | 0.32 | 0.33 | |
| G | 3.22 | 3.19 | 3.21 | 3.18 | 3.08 | 2.96 | 2.63 | 2.12 | 1.32 | 0.90 | 0.69 | 0.53 | 0.40 | 0.38 | 0.32 | 0.35 | 0.28 | 0.34 | 0.28 | 0.35 | 0.28 | 0.33 | 0.27 | 0.36 | 80 ng/mL |
| H | 3.21 | 3.19 | 3.21 | 3.16 | 3.13 | 3.01 | 2.63 | 2.05 | 1.50 | 0.99 | 0.63 | 0.51 | 0.36 | 0.39 | 0.33 | 0.36 | 0.30 | 0.34 | 0.27 | 0.33 | 0.28 | 0.33 | 0.29 | 0.35 | |
| I | 3.22 | 3.19 | 3.20 | 3.18 | 3.12 | 2.99 | 2.67 | 2.10 | 1.44 | 0.91 | 0.67 | 0.51 | 0.38 | 0.38 | 0.30 | 0.36 | 0.30 | 0.34 | 0.28 | 0.33 | 0.28 | 0.32 | 0.28 | 0.34 | |
| J | 0.33 | 0.28 | 0.25 | 0.29 | 0.24 | 0.27 | 0.27 | 0.29 | 0.29 | 0.30 | 0.26 | 0.30 | 0.27 | 0.31 | 0.32 | 0.28 | 0.26 | 0.29 | 0.28 | 0.30 | 0.29 | 0.33 | 0.31 | 0.34 | |
| K | 0.26 | 0.29 | 0.25 | 0.30 | 0.23 | 0.30 | 0.27 | 0.31 | 0.26 | 0.32 | 0.24 | 0.30 | 0.28 | 0.30 | 0.26 | 0.31 | 0.25 | 0.28 | 0.27 | 0.29 | 0.25 | 0.31 | 0.30 | 0.31 | |
| L | 3.17 | 3.12 | 2.97 | 2.49 | 1.64 | 1.06 | 0.63 | 0.47 | 0.31 | 0.31 | 0.39 | 0.27 | 0.24 | 0.27 | 0.24 | 0.27 | 0.24 | 0.27 | 0.24 | 0.29 | 0.23 | 0.27 | 0.25 | 0.31 | 800 ng/mL |
| M | 3.23 | 3.14 | 2.92 | 2.39 | 1.68 | 1.02 | 0.65 | 0.46 | 0.33 | 0.30 | 0.26 | 0.27 | 0.24 | 0.27 | 0.25 | 0.28 | 0.25 | 0.27 | 0.25 | 0.26 | 0.23 | 0.27 | 0.25 | 0.29 | |
| N | 3.19 | 3.15 | 2.96 | 2.42 | 1.27 | 1.00 | 0.64 | 0.45 | 0.33 | 0.30 | 0.25 | 0.25 | 0.24 | 0.26 | 0.23 | 0.25 | 0.25 | 0.28 | 0.28 | 0.26 | 0.25 | 0.30 | 0.29 | 0.29 | |
| O | 0.27 | 0.27 | 0.29 | 0.28 | 0.25 | 0.25 | 0.28 | 0.28 | 0.27 | 0.27 | 0.25 | 0.27 | 0.25 | 0.29 | 0.25 | 0.27 | 0.26 | 0.26 | 0.27 | 0.27 | 0.27 | 0.27 | 0.28 | 0.31 | |
| P | 0.31 | 0.28 | 0.26 | 0.30 | 0.27 | 0.28 | 0.26 | 0.28 | 0.29 | 0.26 | 0.32 | 0.30 | 0.27 | 0.31 | 0.30 | 0.28 | 0.29 | 0.27 | 0.27 | 0.29 | 0.30 | 0.34 | 0.29 | 0.33 | |

Halving dilutions, 10 μg/mL start

FIG. 2B

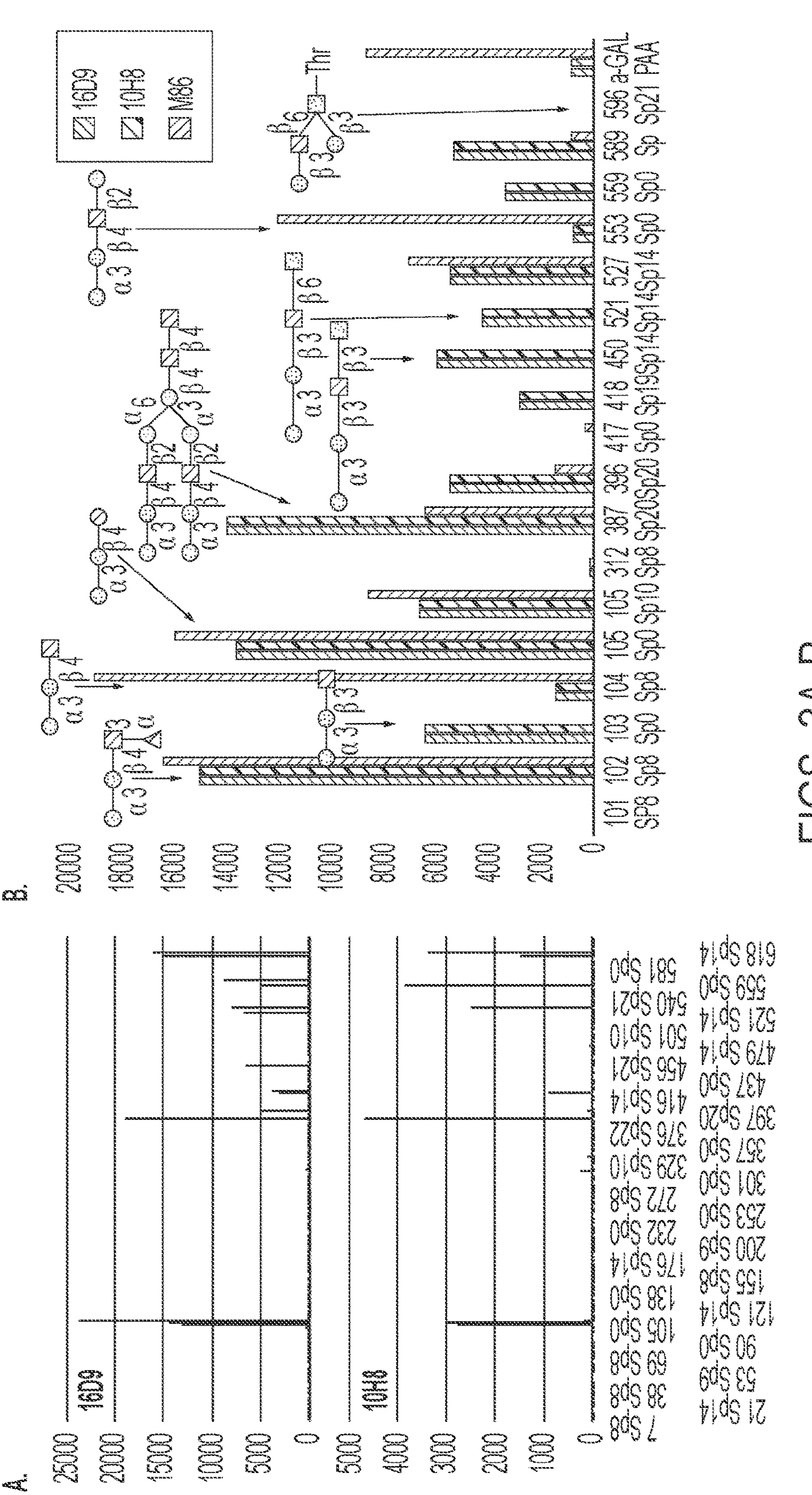
FIGS. 3A-B

SEQUENCE LISTING

```
<160> NUMBER OF SEQ ID NOS: 18

<210> SEQ ID NO 1
<211> LENGTH: 349
<212> TYPE: DNA
<213> ORGANISM: Artificial sequence
<220> FEATURE:
<223> OTHER INFORMATION: Synthetic antibody

<400> SEQUENCE: 1

caggtgcagc tacaacagtg gggcgcagga ctgttgaagc catcggagac cctgtccctc      60

acctgcgctg tctatggtgg gacgttcagt gattacttct atacctggat ccgccagccc     120

ccagggaagg ggctggagtg gattggggaa gtcagtcata ctgggaggac cagctacatc     180

ccgtccctca agagtcgagt caccatgtca gtagacacgt ctaaaaacca gttctccctg     240

aacttgagct ctgtgaccga cgcggacacg gctgtttatt attgtgggag aggtcggggt     300

tacacttgga atgattgggg ccagggaacg ctagtcaccg tctcctcag                 349


<210> SEQ ID NO 2
<211> LENGTH: 349
<212> TYPE: DNA
<213> ORGANISM: Artificial sequence
<220> FEATURE:
<223> OTHER INFORMATION: Synthetic antibody

<400> SEQUENCE: 2

cagtctgccc tgactcagcc tgcctccgtg tctgggtctc ctggacagtc gatcaccatc      60

tcctgcactg gaaccatcac tgacgttggt ggttatgact atgtctcctg gtaccaacaa     120

cacccaggca aagcccccaa actcatcatt ttccttgtca ataatcggcc ctcaggggtt     180

tctgatcgct tctctggctc caagtctggc aacacggcct ccctgaccat ctcagggctc     240

cgggttgagg acgaggctga ttattattgc atgtcatata catgcagcaa cccatataca     300

tgcagcagcc tttatgtctt cggaactggg accaaggtca ccgtcctgg                 349


<210> SEQ ID NO 3
<211> LENGTH: 357
<212> TYPE: DNA
<213> ORGANISM: Artificial sequence
<220> FEATURE:
<223> OTHER INFORMATION: Synthetic antibody

<400> SEQUENCE: 3

caggtgcagc tggtggagtc ggggggaggc gtggtccagc ctgggaggtc cctgagactc      60
```

```
tcctgtgcgg tgtctggatt caccttcagg agctttggca tgcactgggt ccgccaggct    120

ccgggcaagg ggctggagtg ggtggcagtc atatggcatg atggaagtaa caagcactat    180

gcagactccg tgaagggccg attcaccatt tccagagacg actccaagaa caccctgttt    240

ctgcaaatga acagcctgag agccgaggac acggctgtgt attattgtgc gagagaatcg    300

gaggaacagg gaaatatgga cgtctggggc caagggacca cggtcaccgt ctcctca       357
```

<210> SEQ ID NO 4
<211> LENGTH: 340
<212> TYPE: DNA
<213> ORGANISM: Artificial sequence
<220> FEATURE:
<223> OTHER INFORMATION: Synthetic antibody

<400> SEQUENCE: 4

```
gatgttgtga tgactcagtc tccactctcc ctgcccgcca cccttggcca gccggcctcc     60

atctcctgca ggtctagtca tagcctcgtt tacagtaatg gaaacaccta cttgaattgg    120

tttcagcaga ggccaggcca atctccaagg cgcctgtttt ttcaggtttc taaccgggac    180

tctggggtcc cagacagatt cagcggcagt gggtccgtaa ctaatttcac actgaaaatc    240

agcagggtgg aggctgagga tgttggggtc tactactgca tggaaggttc acactggcct    300

ccgtacactt ttggccaggg gaccaggctg gacatcagac                          340
```

<210> SEQ ID NO 5
<211> LENGTH: 116
<212> TYPE: PRT
<213> ORGANISM: Artificial sequence
<220> FEATURE:
<223> OTHER INFORMATION: Synthetic antibody

<400> SEQUENCE: 5

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Thr Phe Ser Asp Tyr
            20                  25                  30

Phe Tyr Thr Trp Ile Arg Gln Pro Pro Gly Lys Gly Leu Glu Trp Ile
        35                  40                  45

Gly Glu Val Ser His Thr Gly Arg Thr Ser Tyr Ile Pro Ser Leu Lys
    50                  55                  60

Ser Arg Val Thr Met Ser Val Asp Thr Ser Lys Asn Gln Phe Ser Leu
65                  70                  75                  80

Asn Leu Ser Ser Val Thr Asp Ala Asp Thr Ala Val Tyr Tyr Cys Gly
                85                  90                  95

Arg Gly Arg Gly Tyr Thr Trp Asn Asp Trp Gly Gln Gly Thr Leu Val
            100                 105                 110

Thr Val Ser Ser
        115
```

<210> SEQ ID NO 6
<211> LENGTH: 116
<212> TYPE: PRT
<213> ORGANISM: Artificial sequence
<220> FEATURE:
<223> OTHER INFORMATION: Synthetic antibody

<400> SEQUENCE: 6

```
Gln Ser Ala Leu Thr Gln Pro Ala Ser Val Ser Gly Ser Pro Gly Gln
1               5                   10                  15
```

```
Ser Ile Thr Ile Ser Cys Thr Gly Thr Ile Thr Asp Val Gly Gly Tyr
            20                  25                  30

Asp Tyr Val Ser Trp Tyr Gln Gln His Pro Gly Lys Ala Pro Lys Leu
        35                  40                  45

Ile Ile Phe Leu Val Asn Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Arg Val Glu Asp Glu Ala Asp Tyr Tyr Cys Met Ser Tyr Thr Cys Ser
                85                  90                  95

Asn Pro Tyr Thr Cys Ser Ser Leu Tyr Val Phe Gly Thr Gly Thr Lys
            100                 105                 110

Val Thr Val Leu
        115


<210> SEQ ID NO 7
<211> LENGTH: 119
<212> TYPE: PRT
<213> ORGANISM: Artificial sequence
<220> FEATURE:
<223> OTHER INFORMATION: Synthetic antibody

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Arg Ser Phe
            20                  25                  30

Gly Met His Trp Val Arg Gln Ala Pro Gly Lys Gly Leu Glu Trp Val
        35                  40                  45

Ala Val Ile Trp His Asp Gly Ser Asn Lys His Tyr Ala Asp Ser Val
    50                  55                  60

Lys Gly Arg Phe Thr Ile Ser Arg Asp Asp Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Glu Ser Glu Glu Gln Gly Asn Met Asp Val Trp Gly Gln Gly
            100                 105                 110

Thr Thr Val Thr Val Ser Ser
        115


<210> SEQ ID NO 8
<211> LENGTH: 113
<212> TYPE: PRT
<213> ORGANISM: Artificial sequence
<220> FEATURE:
<223> OTHER INFORMATION: Synthetic antibody

<400> SEQUENCE: 8

Asp Val Val Met Thr Gln Ser Pro Leu Ser Leu Pro Ala Thr Leu Gly
1               5                   10                  15

Gln Pro Ala Ser Ile Ser Cys Arg Ser Ser His Ser Leu Val Tyr Ser
            20                  25                  30

Asn Gly Asn Thr Tyr Leu Asn Trp Phe Gln Gln Arg Pro Gly Gln Ser
        35                  40                  45

Pro Arg Arg Leu Phe Phe Gln Val Ser Asn Arg Asp Ser Gly Val Pro
    50                  55                  60

Asp Arg Phe Ser Gly Ser Gly Ser Val Thr Asn Phe Thr Leu Lys Ile
65                  70                  75                  80
```

Ser Arg Val Glu Ala Glu Asp Val Gly Val Tyr Tyr Cys Met Glu Gly
85 90 95

Ser His Trp Pro Pro Tyr Thr Phe Gly Gln Gly Thr Arg Leu Asp Ile
100 105 110

Arg

<210> SEQ ID NO 9
<211> LENGTH: 8
<212> TYPE: PRT
<213> ORGANISM: Artificial sequence
<220> FEATURE:
<223> OTHER INFORMATION: Synthetic antibody

<400> SEQUENCE: 9

Gly Gly Thr Phe Ser Asp Tyr Phe
1 5

<210> SEQ ID NO 10
<211> LENGTH: 7
<212> TYPE: PRT
<213> ORGANISM: Artificial sequence
<220> FEATURE:
<223> OTHER INFORMATION: Synthetic antibody

<400> SEQUENCE: 10

Val Ser His Thr Gly Arg Thr
1 5

<210> SEQ ID NO 11
<211> LENGTH: 10
<212> TYPE: PRT
<213> ORGANISM: Artificial sequence
<220> FEATURE:
<223> OTHER INFORMATION: Synthetic antibody

<400> SEQUENCE: 11

Gly Arg Gly Arg Gly Tyr Thr Trp Asn Asp
1 5 10

<210> SEQ ID NO 12
<211> LENGTH: 8
<212> TYPE: PRT
<213> ORGANISM: Artificial sequence
<220> FEATURE:
<223> OTHER INFORMATION: Synthetic antibody

<400> SEQUENCE: 12

Gly Phe Thr Phe Arg Ser Phe Gly
1 5

<210> SEQ ID NO 13
<211> LENGTH: 8
<212> TYPE: PRT
<213> ORGANISM: Artificial sequence
<220> FEATURE:
<223> OTHER INFORMATION: Synthetic antibody

<400> SEQUENCE: 13

Ile Trp His Asp Gly Ser Asn Lys
1 5

<210> SEQ ID NO 14
<211> LENGTH: 12
<212> TYPE: PRT
<213> ORGANISM: Artificial sequence -continued

```
<220> FEATURE:
<223> OTHER INFORMATION: Synthetic antibody

<400> SEQUENCE: 14

Ala Arg Glu Ser Glu Glu Gln Gly Asn Met Asp Val
1               5                   10


<210> SEQ ID NO 15
<211> LENGTH: 9
<212> TYPE: PRT
<213> ORGANISM: Artificial sequence
<220> FEATURE:
<223> OTHER INFORMATION: Synthetic antibody

<400> SEQUENCE: 15

Ile Thr Asp Val Gly Gly Tyr Asp Tyr
1               5


<210> SEQ ID NO 16
<211> LENGTH: 16
<212> TYPE: PRT
<213> ORGANISM: Artificial sequence
<220> FEATURE:
<223> OTHER INFORMATION: Synthetic antibody

<400> SEQUENCE: 16

Met Ser Tyr Thr Cys Ser Asn Pro Tyr Thr Cys Ser Ser Leu Tyr Val
1               5                   10                  15


<210> SEQ ID NO 17
<211> LENGTH: 11
<212> TYPE: PRT
<213> ORGANISM: Artificial sequence
<220> FEATURE:
<223> OTHER INFORMATION: Synthetic antibody

<400> SEQUENCE: 17

His Ser Leu Val Tyr Ser Asn Gly Asn Thr Tyr
1               5                   10


<210> SEQ ID NO 18
<211> LENGTH: 10
<212> TYPE: PRT
<213> ORGANISM: Artificial sequence
<220> FEATURE:
<223> OTHER INFORMATION: Synthetic antibody

<400> SEQUENCE: 18

Met Glu Gly Ser His Trp Pro Pro Tyr Thr
1               5                   10
```

HUMAN IgE MONOCLONAL ANTIBODIES TO ANTIBODIES TO ALPHA-GAL (GALACTOSE-α-1,3-GALACTOSE) AND USES THEREFOR

PRIORITY CLAIM

This application is a national phase application under 35 U.S.C. § 371 of International Application No. PCT/US2021/063107, filed Dec. 13, 2021, which claims benefit of priority to U.S. Provisional Application Ser. No. 63/125,099, filed Dec. 14, 2020, the entire contents of which are hereby incorporated in the entirety.

This invention was made with government support under Grant Number AI130459, awarded by the National Institutes of Health. The Government has certain rights in the invention.

BACKGROUND

1. Field of the Disclosure

The present disclosure relates generally to the fields of medicine, allergies and immunology. More particular, the disclosure relates to human IgE antibodies binding to galactose-α-1,3-galactose.

2. Background

Allergies, also known as allergic diseases, are a number of conditions caused by hypersensitivity of the immune system to typically harmless substances in the environment. These diseases include hay fever, food allergies, atopic dermatitis, allergic asthma, and anaphylaxis. Symptoms may include red eyes, an itchy rash, sneezing, a runny nose, shortness of breath, or swelling. Allergies are common with about 20% of people being affected by allergic rhinitis, about 6% of people having at least one food allergy, and about 20% having atopic dermatitis at some point in time. Unfortunately, rates of many allergic diseases appear to be increasing.

Common allergens include pollen and certain foods. The underlying mechanism involves immunoglobulin E antibodies (IgE), part of the body's immune system, binding to an allergen and then to a receptor on mast cells or basophils where it triggers the release of inflammatory chemicals such as histamine. Treatments for allergies include the avoidance of known allergens and the use of medications such as steroids and antihistamines. In severe reactions injectable adrenaline (epinephrine) is recommended. Allergen immunotherapy, which gradually exposes people to larger and larger amounts of allergen, is useful for some types of allergies such as hay fever and reactions to insect bites. Its use in food allergies is unclear.

Alpha-gal allergy, also known as mammalian meat allergy (MMA), is a reaction to galactose-alpha-1,3-galactose (alpha-gal), whereby the body is overloaded with immunoglobulin E (IgE) antibodies on contact with the carbohydrate. Anti-alpha-gal is a human natural antibody that interacts specifically with the mammalian carbohydrate structure termed the alpha-galactosyl epitope. Bites from certain ticks, which can transfer this carbohydrate to a victim, have been implicated in the development of this delayed allergic response to consumption of mammalian meat products. Improved methods for the treatment of this condition are very much in need.

SUMMARY

Thus, in accordance with the present disclosure, there is provided a method of:

- detecting galactose-α-1,3-galactose (alpha-gal) in a sample comprising (a) contacting a sample with an antibody or antibody fragment having clone-paired heavy and light chain CDR sequences from Tables 3 and 4, respectively; and (b) detecting alpha-gal in said sample by binding of said antibody or antibody fragment to alpha-gal in said sample, such as where the sample is a biologic fluid, such has a biologic culture, media or culture supernatant, blood, sputum, tears, saliva, mucous or serum, semen, cervical or vaginal secretions, amniotic fluid, placental tissues, urine, exudate, transudate, tissue scrapings or feces, a food or tissue sample, a drug formulation, a biologic therapeutic formulation or a vaccine stock; or
- detecting IgE anti-galactose-α-1,3-galactose (alpha-gal) antibodies in a sample, such as one from a living subject, comprising (a) contacting a sample suspected IgE anti-alpha gal antibodies with alpha-gal in a competitive assay with an antibody or antibody fragment having clone-paired heavy and light chain CDR sequences from Tables 3 and 4, respectively; and (b) detecting competition for binding of alpha-gal by a suspected IgE anti-alpha gal in said sample by an antibody or antibody fragment having clone-paired heavy and light chain CDR sequences from Tables 3 and 4, respectively.

Detection may comprise ELISA, RIA, lateral flow assay or Western blot. The method may further comprising performing steps (a) and (b) a second time and determining a change in alpha-gal levels as compared to the first assay. The antibody or antibody fragment may be encoded by clone-paired variable sequences as set forth in Table 1, be encoded by light and heavy chain variable sequences having 70%, 80%, or 90% identity to clone-paired variable sequences as set forth in Table 1, or be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment.

In another embodiment, there is provided a method of preventing or treating an alpha-gal-related allergic reaction in a subject comprising delivering to said subject an IgG antibody or antibody fragment having clone-paired heavy and light chain CDR sequences from Tables 3 and 4, respectively. The antibody or antibody fragment may be encoded by clone-paired light and heavy chain variable sequences as set forth in Table 1, may be encoded by clone-paired light and heavy chain variable sequences having 95% identity to as set forth in Table 1, or may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprises light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment, may comprise an Fc portion mutated to alter (eliminate or enhance) FcR interactions, to increase half-life and/or increase therapeutic efficacy or is glycan modified to alter (eliminate or enhance) FcR interactions, may have a Fc portion containing a LALA, LALA-PG, N297, GASD/ALIE, DHS, YTE or LS mutation, such as where glycan modification that is an enzymatic or chemical addition or removes of glycans or results from expression in a cell line engineered with a defined glycosylating pattern. The antibody may be a chimeric antibody or a bispecific antibody. Delivering may comprise antibody or antibody fragment administration, or genetic delivery with an RNA or DNA sequence or vector encoding the antibody or antibody fragment.

Also provided is a monoclonal antibody, wherein the antibody or antibody fragment is characterized by clone-paired heavy and light chain CDR sequences from Tables 3 and 4, respectively. The antibody or antibody fragment may be encoded by light and heavy chain variable sequences according to clone-paired sequences from Table 1, may be encoded by light and heavy chain variable sequences having at least 70%, 80%, or 90% identity to clone-paired sequences from Table 1, or may be encoded by light and heavy chain variable sequences having at least 95% identity to clone-paired sequences from Table 1. The antibody or antibody fragment may comprise light and heavy chain variable sequences according to clone-paired sequences from Table 2, or may comprise light and heavy chain variable sequences having 70%, 80%, 90% or 95% identity to clone-paired sequences from Table 2. The antibody fragment may be a recombinant scFv (single chain fragment variable) antibody, Fab fragment, $F(ab')_2$ fragment, or Fv fragment. The antibody may be a chimeric antibody, or is bispecific antibody. The antibody may bean IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody or antibody fragment may further comprise a cell penetrating peptide and/or is an intrabody.

In yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired light and heavy chain variable sequences as set forth in Table 1, may be encoded by clone-paired light and heavy chain variable sequences having 95% identity to as set forth in Table 1, or may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprises light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment. The antibody may be a chimeric antibody or a bispecific antibody. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern.

In still yet another embodiment, there is provided a vaccine formulation comprising one or more IgG antibodies or antibody fragments characterized by clone-paired heavy and light chain CDR sequences from Tables 3 and 4, respectively. The antibody or antibody fragment may be encoded by clone-paired light and heavy chain variable sequences as set forth in Table 1, may be encoded by clone-paired light and heavy chain variable sequences having 95% identity to as set forth in Table 1, or may be encoded by light and heavy chain variable sequences having 70%, 80%, or 90% identity to clone-paired sequences from Table 1. The antibody or antibody fragment may comprise light and heavy chain variable sequences according to clone-paired sequences from Table 2, may comprises light and heavy chain variable sequences having 70%, 80% or 90% identity to clone-paired sequences from Table 2, or may comprise light and heavy chain variable sequences having 95% identity to clone-paired sequences from Table 2. At least one of said antibody fragments may be a recombinant scFv (single chain fragment variable) antibody, Fab fragment, $F(ab')_2$ fragment, or Fv fragment. At least one of said antibodies is a chimeric antibody or is bispecific antibody. At least one of said antibodies or fragments may comprise an Fc portion mutated to alter (eliminate or enhance) FcR interactions, to increase half-life and/or increase therapeutic efficacy, such as a LALA, LALA-PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern.

A further embodiment relates to a vaccine formulation comprising one or more expression vectors encoding a first antibody or antibody fragment as defined here. The first antibody or antibody fragment may be encoded by clone-paired light and heavy chain variable sequences as set forth in Table 1, may be encoded by clone-paired light and heavy chain variable sequences having 95% identity to as set forth in Table 1, or may be encoded by light and heavy chain variable sequences having 70%, 80%, or 90% identity to clone-paired sequences from Table 1. The first antibody or antibody fragment may comprise light and heavy chain variable sequences according to clone-paired sequences from Table 2, may comprises light and heavy chain variable sequences having 70%, 80% or 90% identity to clone-paired sequences from Table 2, or may comprise light and heavy chain variable sequences having 95% identity to clone-paired sequences from Table 2. The expression vector(s) may be Sindbis virus or VEE vector(s). The vaccine formulation may be formulated for delivery by needle injection, jet injection, or electroporation. The vaccine formulation may further comprise one or more expression vectors encoding for a second antibody or antibody fragment, such as a distinct antibody from the first antibody.

Also provided is human monoclonal antibody or antibody fragment, or hybridoma or engineered cell producing the same, wherein said antibody binds to galactose-α-1,3-galactose.

An additional embodiment comprises a method of desensitizing a subject to galactose-α-1,3-galactose (alpha-gal) comprising (a) administering to said subject galactose-α-1,3-galactose (alpha-gal); and (b) administering to said subject an IgG antibody that has a binding specificity to galactose-α-1,3-galactose (alpha-gal) obtained from an IgE antibody or antibody fragment characterized by clone-paired heavy and light chain CDR sequences from Tables 3 and 4, respectively. The IgG antibody or antibody fragment may be encoded by clone-paired light and heavy chain variable sequences as set forth in Table 1, may be encoded by clone-paired light and heavy chain variable sequences having 95% identity to as set forth in Table 1, or may be encoded by light and heavy chain variable sequences having 70%, 80%, or 90% identity to clone-paired sequences from Table 1. The IgG antibody or antibody fragment may comprise light and heavy chain variable sequences according to clone-paired sequences from Table 2, may comprises light and heavy chain variable sequences having 70%, 80% or 90% identity to clone-paired sequences from Table 2, or may comprise light and heavy chain variable sequences having 95% identity to clone-paired sequences from Table 2. The allergen and said IgG antibody or fragment thereof may be mixed together prior to administering or may be administered to said subject separately. The allergen and said IgG antibody or fragment thereof may be administered to said subject multiple times. The subject may be a human or a non-human mammal. The allergen may be administered with an adjuvant.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-C. Human alpha-gal-specific IgE mAb characterization. Half maximal effective concentration ($EC_{50}$) for binding to cetuximab and bovine thyroglobulin (BTG) were determined (FIG. 1A). Cetuximab: 16D9=20 ng/mL; 10H8=78 ng/mL and BTG: 16D9=16 ng/mL; 10H8=72 ng/mL. Immunoblotting patterns for cetuximab and BTG (10 mg & 5 mg) are shown for 16D9 and 10H8 (FIG. 1B). Low and high magnification of porcine kidney stained with IgE mAb 16D9 in immunohistochemistry (FIG. 1C).

FIGS. 2A-B. Comparative $EC_{50}$ binding of mAbs 16D9, 10H8, M86 to Cetuximab & Bovine thyroglobulin (BTG). Approximate half maximal effective concentration ($EC_{50}$) for binding to cetuximab (FIG. 2A) and BTG (FIG. 2B) were estimated to compare strength of binding. Human IgE mAb 16D9 bound to both cetuximab and BTG with approximately 100-fold greater affinity than commercially available anti alpha-gal murine mAb M86. Human IgE mAb 10H8 bound to both cetuximab and BTG with approximately 10-fold greater affinity than commercially available anti alpha-gal murine mAb M86.

FIGS. 3A-B. Epitope mapping using glycan array technology. Glycan array epitope mapping was performed on human IgE mAbs 10H8 and 16D9 with hits FIG. 3A. Top glycan hits shared by 16D9 and 10H8 are shown in FIG. 3B. Extensively characterized murine anti alpha-gal mAb M86 was used as a control to show that significant differences in binding specificity occur between this reagent antibody and the pathogenic naturally-occurring human IgE mAbs.

DESCRIPTION OF ILLUSTRATIVE EMBODIMENTS

As discussed above, alpha-gal allergy or MMA is a significant allergic reaction to galactose-alpha-1,3-galactose (alpha-gal). Subject suffering from this condition are unable to safely consume certain mammalian meat products. At present there are only limited methods of mitigating the effects of MMA and improved methods for the treatment or eliminating this condition are needed.

The inventor has generated two human hybridomas that secrete IgE monoclonal antibodies, 16D9 and 10H8, which bind the alpha-gal disaccharide, galactose-α-1,3-galactose. These antibodies were generated from an individual with allergy to red meat, originating from tick bites. They have been tested against and bind strongly to the alpha-gal containing cancer drug cetuximab, as well as bovine thyroglobulin, the gold standard for assaying alpha-gal IgE in human serum. These monoclonal antibodies are likely the only known human antibodies that bind alpha-gal. They can be used as a control reagent for standardizing serum assays, such as those performed on patients being evaluated for meat allergy. They can also be used to assay human use materials for the presence of the antigen, which frequently contaminate human vaccines and therapeutics, resulting in allergic reactions in individuals with occult meat allergy (such as the varicella zoster vaccine and the cancer drug cetuximab). Finally, IgG switched variant mAbs, made from the variable sequences, are useful as blocking therapeutics.

These and other aspects of the disclosure are described in detail below.

I. IGE ANTIBODIES AND ALLERGIC REACTIONS

A. Biology

Immunoglobulin E (IgE), first discovered in 1966, is a kind of antibody (or immunoglobulin (Ig) "isotype") that has only been found in mammals. IgE is synthesised by plasma cells. Monomers of IgE consist of two heavy chains (ε chain) and two light chains, with the F chain containing 4 Ig-like constant domains (Cε1-Cε4). IgE's main function is immunity to parasites such as helminths like *Schistosoma mansoni, Trichinella spiralis*, and *Fasciola hepatica*. IgE is utilized during immune defense against certain protozoan parasites such as *Plasmodium falciparum*.

IgE also has an essential role in type I hypersensitivity, which manifests in various allergic diseases, such as allergic asthma, most types of sinusitis, allergic rhinitis, food allergies, and specific types of chronic urticaria and atopic dermatitis. IgE also plays a pivotal role in responses to allergens, such as: anaphylactic drugs, bee stings, and antigen preparations used in desensitization immunotherapy.

Although IgE is typically the least abundant isotype-blood serum IgE levels in a normal ("non-atopic") individual are only 0.05% of the Ig concentration, compared to 75% for the IgGs at 10 mg/ml, which are the isotypes responsible for most of the classical adaptive immune response—it is capable of triggering the most powerful inflammatory reactions.

IgE primes the IgE-mediated allergic response by binding to Fc receptors found on the surface of mast cells and basophils. Fc receptors are also found on eosinophils, monocytes, macrophages and platelets in humans. There are two types of Fcε receptors, FcεRI (type I Fcε receptor), the high-affinity IgE receptor, and FcεRII (type II Fcε receptor), also known as CD23, the low-affinity IgE receptor. IgE can upregulate the expression of both types of Fcε receptors. FcεRI is expressed on mast cells, basophils, and the antigen-presenting dendritic cells in both mice and humans. Binding of antigens to IgE already bound by the FcεRI on mast cells causes cross-linking of the bound IgE and the aggregation of the underlying FcεRI, leading to the degranulation and the release of mediators from the cells. Basophils, upon the cross-linking of their surface IgE by antigens, release type 2 cytokines like interleukin-4 (IL-4) and interleukin-13 (IL-13) and other inflammatory mediators. The low-affinity receptor (FcεRII) is always expressed on B cells; but IL-4 can induce its expression on the surfaces of macrophages, eosinophils, platelets, and some T cells.

There is much speculation into what physiological benefits IgE contributes, and, so far, circumstantial evidence in animal models and statistical population trends have hinted that IgE may be beneficial in fighting gut parasites such as *Schistosoma mansoni*, but this has not been conclusively proven in humans. Epidemiological research shows that IgE level is increased when infected by *Schistosoma mansoni, Necator americanus*, and nematodes in human. It is most likely beneficial in removal of hookworms from the lung.

Although it is not yet well understood, IgE may play an important role in the immune system's recognition of cancer, in which the stimulation of a strong cytotoxic response against cells displaying only small amounts of early cancer markers would be beneficial. If this were the case, anti-IgE treatments such as omalizumab (for allergies) might have some undesirable side effects. However, a recent study, which was performed based on pooled analysis using comprehensive data from 67 phase I to IV clinical trials of omalizumab in various indications, concluded that a causal relationship between omalizumab therapy and malignancy is unlikely.

Atopic individuals can have up to 10 times the normal level of IgE in their blood (as do sufferers of hyper-IgE syndrome). However, this may not be a requirement for symptoms to occur as has been seen in asthmatics with normal IgE levels in their blood—recent research has shown that IgE production can occur locally in the nasal mucosa.

IgE that can specifically recognize an "allergen" (typically this is a protein, such as a peanut allergen, grass or ragweed pollen, etc.) has a unique long-lived interaction with its high-affinity receptor FcεRI so that basophils and mast cells, capable of mediating inflammatory reactions, become "primed", ready to release chemicals like histamine, leukotrienes, and certain interleukins. These chemicals cause many of the symptoms are associated with allergy, such as airway constriction in asthma, local inflammation in eczema, increased mucus secretion in allergic rhinitis, and increased vascular permeability, it is presumed, to allow other immune cells to gain access to tissues, but which can lead to a potentially fatal drop in blood pressure as in anaphylaxis. IgE is known to be elevated in various autoimmune disorders such as lupus (SLE), rheumatoid arthritis (RA) and psoriasis, and is theorized to be of pathogenetic importance in RA and SLE by eliciting a hypersensitivity reaction.

Regulation of IgE levels through control of B cell differentiation to antibody-secreting plasma cells is thought to involve the "low-affinity" receptor FcεRII, or CD23. CD23 may also allow facilitated antigen presentation, an IgE-dependent mechanism whereby B cells expressing CD23 are able to present allergen to (and stimulate) specific T helper cells, causing the perpetuation of a Th2 response, one of the hallmarks of which is the production of more antibodies.

Diagnosis of allergy is most often done by reviewing a person's medical history and finds a positive result for the presence of allergen specific IgE when conducting a skin or blood test. Specific IgE testing is the proven test for allergy detection; evidence does not show that indiscriminate IgE testing or testing for immunoglobulin G (IgG) can support allergy diagnosis.

B. Red Meat Allergens

Alpha-gal allergy, also known as mammalian meat allergy (MMA), is a reaction to galactose-α-1,3-galactose (alpha-gal), whereby the body is overloaded with immunoglobulin E (IgE) antibodies on contact with the carbohydrate. Anti-gal is a human natural antibody that interacts specifically with the mammalian carbohydrate structure gal alpha 1-3Gal beta 1-4GlcNAc-R, termed, the alpha-galactosyl epitope.

Bites from certain ticks, such as the lone star tick (*Am. americanum*) in the U.S., and the paralysis tick in Australia, which can transfer this carbohydrate to a victim, have been implicated in the development of this delayed allergic response to consumption of mammalian meat products. Individuals with alpha-gal allergy do not need to become strict vegetarians, because poultry, fish, and in rare cases for some people, lean meat such as venison does not trigger a reaction.

Alpha-gal allergy has been reported in 17 countries on all 6 continents where humans are bitten by ticks, particularly the United States and Australia. As at November 2019 Australia has the highest rate of mammalian meat allergy and tick anaphylaxis in the world. In the US, the allergy most often occurs in the central and southern regions, which corresponds to the distribution of the lone star tick. In the Southern United States, where the tick is most prevalent, allergy rates are 32% higher than elsewhere. However, as doctors are not required to report the number of patients with alpha-gal allergy, the true number of affected individuals is unknown. Alpha-gal has also been shown to exist in the saliva of *Ix. scapularis* but not *Am. maculatum.*

A typical allergic reaction to alpha-gal has a delayed onset, occurring 3-8 hours after the consumption of mammalian meat products, in contrast to the typical rapid onset of most food allergies. After the delayed onset, the allergic response is like most food allergies, and especially an IgE-mediated allergy, including severe whole-body itching, hives, angioedema, gastrointestinal upset, and possible anaphylaxis. In 70% of cases the reaction is accompanied by respiratory distress and as such is particularly harmful to those with asthma.

Alpha-gal allergies are the first known food allergies that present the possibility of delayed anaphylaxis. It is also the first known food-related allergy associated with a carbohydrate, rather than a protein. Other mammalian products containing alpha-gal other than meat such as milk and gelatin may also trigger an allergic reaction.

Alpha-gal allergies develop after a person has been bitten by the lone star tick in the United States, the European castor bean tick, the paralysis tick and *Ixodes* (*Endopalpiger*) *australiensis* in Australia, *Haemaphysalis longicornis* in Japan, and a currently unknown tick in South Africa, possibly *Amblyomma hebraeum*. Alpha-gal is not naturally present in apes, Old World monkeys, or humans, but is in all other mammals. If a tick feeds on another mammal, the alpha-gal remains in its alimentary tract. The tick then injects the alpha-gal into a person's skin, which causes the immune system to release a flood of IgE antibodies to fight the foreign carbohydrate. Researchers still do not know which specific component of tick saliva causes the reaction.

Alpha-gal is present in the anticancer drug cetuximab, as well as the intravenous fluid replacements Gelofusine and Haemaccel. Blood thinners derived from porcine intestine and replacement heart valves derived from porcine tissue may also contain alpha-gal. At least one instance of a man with an alpha-gal allergy going into anaphylaxis after receiving a heart valve transplant has been reported. Some researchers have suggested that the alpha-gal in pig's tissue that surgeons use for xenografts might contribute to organ rejection.

Recent research has shown that saliva from the lone star tick contains alpha-gal, and that saliva is injected into the blood stream. The immune system then releases IgE antibodies to fight this foreign sugar. After this reaction, the future intake of mammal meat with the same alpha-gal causes an allergic reaction. Symptoms of the allergy reaction are caused by too many IgE antibodies attacking the allergen, in this case the alpha-gal.

A traditional skin-prick allergy test for allergy to meat may give a false-negative answer. Determination of specific IgE to alpha-gal testing is commercially available, as well as IgE testing to specific red meats. Skin and basophil activation tests with cetuximab are the most sensitive, but high costs limit their use.

Unlike most food allergies, in some people, the alpha-gal allergy may recede over time, as long as the person is not bitten by another tick. The recovery period can take 8 months to 5 years. So far, only two successful desensitizations have been performed on patients with an alpha-gal allergy.

II. MONOCLONAL ANTIBODIES AND PRODUCTION THEREOF

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}$H when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to alpha-gal will have several applications. These include the production of diagnostic kits for use in detecting and diagnosing alpha-gal contamination and alpha-gal antibody levels in subjects, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce alpha-gal-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. Unlike the situation in protein antigens where the sequence and/or conformation of the amino acids that make up the protein determine the epitope, alpha-gal is a disaccharide glycan that exist of many proteins.

The term "epitope" refers to a site on an antigen to which B and/or T cells respond. The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-alpha-gal antibody, the above-described binding methodology is performed in two orientations: In a first orientation, the reference antibody is allowed to bind to alpha-gal under saturating conditions followed by assessment of binding of the test antibody to the complex. In a second orientation, the test antibody is allowed to bind to the alpha-gal molecule under saturating conditions followed by assessment of binding of the reference antibody to the complex. If, in both orientations, only the first (saturating) antibody is capable of binding to the alpha-gal, then it is concluded that the test antibody and the reference antibody compete for binding to alpha-gal. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., *Cancer Res.* 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example, with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example, antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002), J. Biol. Chem. 277(30): 26733-26740; Davies J. et al. (2001), Biotechnology & Bioengineering 74(4): 288-294). Methods of altering carbohydrate contents are known to those skilled in the art, see, e.g., Wallick, S. C. et al. (1988), J. Exp. Med. 168(3): 1099-1109; Tao, M. H. et al. (1989), J. Immunol. 143(8): 2595-2601; Routledge, E. G. et al. (1995), Transplantation 60(8):847-53; Elliott, S. et al. (2003), Nature Biotechnol. 21:414-21; Shields, R. L. et al. (2002), J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the mAbs, or single-chain immunoglobulins producible, for example, via recombinant means. F(ab') antibody derivatives are monovalent, while $F(ab')_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb but were completely devoid of enhancing activity. LALA mutations of this nature are therefore contemplated in the context of the presently disclosed antibodies.

Class Switch. The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency. Modifications in the Fc region can be introduced to extend the in vivo half-life of the antibody, or to alter Fc mediated functions such as complement activation, antibody dependent cellular cytotoxicity (ADCC), and FcR-mediated phagocytosis.

Of central importance to the present disclosure is isotype modification involving changing a naturally occurring human IgE isotype variable sequence to an IgG isotype. By making this unnatural modification of the IgE antibody, a pathogenic molecule can be made to possess therapeutic functions. Aside from the theoretical benefit that IgE isotype antibodies may have in control of helminth infections, IgE antibodies are necessary for causing IgE-mediated allergy. The function of an IgE antibody is conveyed through its Fc region, which directs binding of the antibody to specific Fc receptors on various cells. By changing a natural human IgE to an IgG, one completely alters the Fc receptors that can be engaged—this has never been shown to occur naturally in humans since the IgG isotypes are deleted from the B cell DNA when it class-switched to IgE. It is the IgE antibody's ability to bind the Fc receptors, FcεRI and FcεRII, which endow its pathogenic function. By engineering a human IgE variable sequence into an IgG antibody isotype, the pathogenic molecule can no longer perform its harmful functions. Additionally, the engineered IgG antibody can then provide new, therapeutic functions through engagement with various Fcγ receptors, such as those found on the mast cell, including FcγRIIB. IgG antibodies that bind FcγRIIB on the surface of mast cells result in inhibitory signaling and inhibition of mediator release. For example, an allergen specific IgE antibody bound to FcεRI on mast cells will signal the release of inflammatory mediators upon binding its specific allergen—resulting in the diseases associated with allergy. However, an IgG made from the allergen-specific IgE variable sequences would bind FcγRIIB on mast cells and inhibit mediator release upon binding the specific disease inciting allergen.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. 0-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.,* 22 (10), 1302-1306, 2004; Chennamsetty et al., *PNAS,* 106 (29), 11937-11942, 2009; Voynov et al., *Biocon. Chem.,* 21(2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning Calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., $F(ab')_2$ bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175: 217-225 (1992) describe the production of a humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol.* 16, 677-681 (1998). doi:10.1038/nbt0798-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters.* 2005; 579: 3264; Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., *Science,* 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-$(X1)_n$-VD2-$(X2)_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises (a) a first Fab molecule which specifically binds to a first antigen (b) a second Fab molecule which specifically binds to a second antigen, and wherein the variable domains VL and VH of the Fab light chain and the Fab heavy chain are replaced by each other, wherein the first antigen is an activating T cell antigen and the second antigen is a target cell antigen, or the first antigen is a target cell antigen and the second antigen is an activating T cell antigen; and wherein i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 ξ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/anti-viral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/antiviral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/antiviral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. TREATMENT/PREVENTION OF ALLERGIC REACTION

A. Formulation and Administration

The present disclosure provides pharmaceutical compositions comprising anti-alpha-gal antibodies and alpha-gal antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rheniumis$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting alpha-gal containing molecules. While such methods can be applied in a traditional sense, another use will be in quality control and monitoring of vaccine and other antigen stocks, where antibodies according to the present disclosure can be used to assess the amount of alpha-gal in vaccine stocks. Alternatively, the methods may be used to screen various antibodies for appropriate/desired reactivity profiles.

Other immunodetection methods include specific assays for determining the presence of anti-alpha-gal antibodies in a subject. A wide variety of assay formats are contemplated, but specifically those that would be used to detect anti-alpha-gal antibodies in a fluid obtained from a subject, such as saliva, blood, plasma, sputum, semen or urine. The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of anti-alpha-gal antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing anti-alpha-gal antibodies and contacting the sample with a first antibody in accordance with the present disclosure, as the case may be, under conditions effective to allow the formation of immunocomplexes.

These methods include methods for purifying anti-alpha-gal antibodies from a sample. The antibody will preferably be linked to a solid support, such as in the form of a column matrix, and the sample suspected of containing the anti-alpha-gal antibodies will be applied to the immobilized antibody. The unwanted components will be washed from the column, leaving the anti-alpha-gal antibodies immunocomplexed to the immobilized antibody, which is then collected by removing the organism or antigen from the column.

The immunobinding methods also include methods for detecting and quantifying the amount of anti-alpha-gal antibodies in a sample and the detection and quantification of any immune complexes formed during the binding process. Here, one would obtain a sample suspected of containing anti-alpha-gal antibodies and contact the sample with an antibody that competes with anti-alpha-gal antibodies, followed by detecting and quantifying the amount of immune complexes formed under the specific conditions. In terms of antigen detection, the biological sample analyzed may be any sample that is suspected of containing anti-alpha-gal antibodies, such as a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to alpha-gal present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, for example, with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the anti-alpha-gal antibodies is added to the wells. After binding and washing to remove non-specifically bound immune complexes, the bound antigen may be detected. Detection may be achieved by the addition of another anti-alpha-gal antibody that is linked to a detectable label. This type of ELISA is a simple "sandwich ELISA." Detection may also be achieved by the addition of a second anti-alpha-gal antibodies, followed by the addition of a third antibody that has binding affinity for the second antibody, with the third antibody being linked to a detectable label.

In another exemplary ELISA, the samples suspected of containing the alpha-gal are immobilized onto the well surface and then contacted with the anti-alpha-gal antibodies of the disclosure. After binding and washing to remove non-specifically bound immune complexes, the bound anti-alpha-gal antibodies are detected. Where the initial anti-alpha-gal antibodies are linked to a detectable label, the immune complexes may be detected directly. Again, the immune complexes may be detected using a second antibody that has binding affinity for the first anti-alpha-gal antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of anti-alpha-gal antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled anti-alpha-gal antibodies to determine the amount of anti-alpha-gal antibodies in a sample. The basic format would include contacting a known amount of anti-alpha-gal antibody (linked to a detectable label) with sample containing anti-alpha-gal antibodies, such as attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Kits

In still further embodiments, the present disclosure concerns kits for use with the methods described above. As the antibodies may be used to detect alpha-gal or anti-alpha-gal antibodies may be included in the kit. The kits will thus comprise, in suitable container means, a first antibody that binds to alpha-gal, and optionally an immunodetection reagent.

In certain embodiments, the anti-alpha-gal antibodies may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the alpha-gal or anti-alpha-gal antibodies, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

Antibodies and fragments thereof as described in the present disclosure may also be used in a kit for monitoring allergic reaction by detecting the presence of anti-alpha-gal antibodies.

E. Vaccine and Antigen Quality Control Assays

The present disclosure also contemplates the use of antibodies and antibody fragments as described herein for use in assessing the presence of an alpha-gal antigen in a sample. Medicinal products like vaccines, biologics and chemical drugs can contain contaminants including alpha-gal and have the capacity to vary widely from preparation to preparation. They are also administered to healthy as well as diseased individuals, including children, and thus a strong emphasis must be placed on their quality to ensure, to the greatest extent possible, that they are efficacious in preventing or treating life-threatening disease, without themselves causing harm.

The increasing globalization in the production and distribution of medicines has opened new possibilities to better manage public health concerns but has also raised questions about the equivalence and interchangeability of medicine procured across a variety of sources. International standardization of starting materials, of production and quality control testing, and the setting of high expectations for regulatory oversight on the way these products are manufactured and used, have thus been the cornerstone for continued success. It remains a field in constant change, and continuous technical advances in the field offer a promise of developing potent new weapons against the oldest public health threats, as well as new ones, but also put a great pressure on manufacturers, regulatory authorities, and the wider medical community to ensure that products continue to meet the highest standards of quality attainable.

Thus, one may obtain a medicine from any source or at any point during a manufacturing process. The quality control processes may therefore begin with preparing a sample for an immunoassay that identifies binding of an antibody or fragment disclosed herein to an alpha-gal antigen. Such immunoassays are disclosed elsewhere in this document, and standards for finding the sample to contain alpha-gal antigen may be established by regulatory agencies.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Human hybridoma generation and IgE mAb purification. IgE-secreting human hybridomas were generated using methodology that was recently described in great detail (Wurth et al., 2018). Previously cryopreserved samples were thawed, washed, and counted before plating. For every 2 million viable cells, the following was added: 30 ml of prefusion medium (ClonaCell-HY 03801; Stemcell Technologies), 20 ml of CpG stock (2.5 mg/ml; ODN 2006), 1 μl each of mouse anti-human kappa (Southern Biotech; 9230-01) and mouse anti-human lambda (Southern Biotech; 9180-01), and 1 million gamma-irradiated NIH3T3 fibroblast line genetically engineered to constitutively express cell-surface human CD154 (CD40 ligand), secreted human B cell activating factor (BAFF) and human IL-21. The mixture then was plated into 96-well flat bottom culture plates at 300 ml/well, and incubated at 37° C. with 5% $CO_2$ for 7 days, prior to screening for IgE secretion using an ELISA. Omalizumab was used as a capture antibody, coating 384-well black ELISA plates at a concentration of 10 μg/ml. After blocking, 100 μl of supernatant was transferred from each well of the 96-well plates containing B cell lines, using a VIAFLO-384 electronic pipetting device (Integra Bioscisences). Secondary antibody (mouse anti-human IgE Fc; Southern biotech, 9160-05) was applied at a 1:1,000 dilution in blocking solution using 25 μl/well. After 10 washes with PBS, fluorogenic peroxidase substrate solution (QuantaBlu; Thermo Scientific 15162) was added at 25 μl/well, as per manufacturer instructions. Relative fluorescence intensity was determination on a Molecular Devices plate reader. Wells are counted as positive if the relative fluorescence intensity is >5 times background. IgE B cell frequencies then are expressed as the number of IgE positive wells per 10 million peripheral blood mononuclear cells. A secondary screen, by direct ELISA using the human therapeutic mAb cetuximab, was performed to allow for the identification of alpha-gal specific B cell cultures.

HMMA2.5 non-secreting myeloma cells were counted and suspended in cytofusion medium composed of 300 mM sorbitol, 1.0 mg/ml of bovine serum albumin, 0.1 mM calcium acetate, and 0.5 mM magnesium acetate. Cells from IgE positive wells were pipetted gently into microcentrifuge tubes containing 1 ml of cytofusion medium. B cells and HMMA2.5 cells were washed three times in cytofusion medium to ensure equilibration. HMMA2.5 cells were then suspended in cytofusion medium to achieve a concentration of 10 million cells/ml. The HMMA2.5 cell suspension was added to each sample tube and the mixture pipetted into cuvettes (BTX, 450125). Cytofusion was performed using a BTX cuvette holder (BTX Safety stand, model 630B) with a BTX ECM 2001 generator (BTX; 45-0080) programed to run with following settings: a prefusion AC current of 70 V for 40 s, followed by a DC current pulse of 360 V for 0.04 ms and then a post-fusion AC current of 40 V for 9 s. After fusion the content of each cuvette was then added to 20 ml of hypoxanthine-aminopterin-thymidine (HAT) medium containing ouabain, composed of the following: 500 ml of post-fusion medium (Stemcell Technologies, 03805), one vial 50×HAT (Sigma, H0262), and 150 μl of a 1 mg/ml stock of ouabain (Sigma, 013K0750). Fusion products then were plated into 384-well plates and incubated for 14 days before screening hybridomas for IgE antibody production by ELISA.

Wells containing hybridomas producing IgE antibodies were cloned biologically by indexed single cell flow cytometric sorting into 384-well culture plates. Once clonality was achieved, each hybridoma was expanded in post-fusion medium in 75-cm$^2$ flasks. MAb was expressed by large-scale growth of the hybridoma in serum free medium (Gibco Hybridoma-SFM; Invitrogen, 12045084) in 225-cm$^2$ flasks. IgE antibody was then purified by immunoaffinity chromatography (Omalizumab covalently coupled to GE Healthcare NHS activated HiTRAP; 17-0717-01) and visualized by SDS-PAGE for purity.

Alpha-gal specificity and EC50 by ELISA. The final allergen-specificity of each IgE mAb was confirmed/defined using Thermo/Phadia ImmunoCAP (alpha-gal, o215). Medium from cultured IgE secreting human hybridoma clones were diluted 1:1000 in normal saline prior to measurement on ImmunoCAP devise—performed at the Johns Hopkins Allergy and Clinical Immunology Reference Laboratory. Only IgE mAbs 10H8 and 16D9 returned with positive values and were studied further for alpha-gal binding.

Half maximal effective concentration ($EC_{50}$s) were obtained for alpha-gal binding of human IgE mAbs 10H8 and 16D9, as well as recombinant human IgE mAb M86, which was purchased from Absolute antibody (Ab00532-14.0). Cetuximab or bovine thyroglobulin were used to coat 384-well ELISA plates at a concentration of 25 μg/ml. After blocking with 2% ovalbumin (Fisher, 40045) for 1 h, 25 ml of IgE antibody was added as a dilution series in triplicate, starting at a concentration of 10 μg/ml. After a 1 h incubation at room temperature and washing five times, secondary antibody (mouse anti-human IgE Fc; Southern biotech, 9160-05) was applied at a 1:1,000 dilution in ovalbumin blocking solution using 25 μl/well. After 10 washes with PBS, fluorogenic peroxidase substrate solution (QuantaBlu; Thermo Scientific 15162) or TMB (Thermo, 34029) was added at 25 μl/well, as per manufacturer instructions. Relative fluorescence intensity or optical density was determination on a Molecular Devices plate reader.

Western blotting and immunohistochemistry. To visualize the molecular size of the protein which possesses the alpha-gal glycan, 5 and 10 μg of cetuximab and BTG were subjected to SDS-PAGE under reducing and denaturing conditions. Gels were then transferred to nitrocellulose membranes to prepare for blotting. After blocking membranes in 2% ovalbumin overnight, antibodies 16D9 or 10H8 were added at 1:1,000 as 10 mL in block. After washing in PBS, secondary antibody (mouse anti-human IgE Fc; Southern biotech, 9160-05) was applied at a 1:1,000 dilution in ovalbumin block. Finally, after washing overnight in PBS, chemiluminescent substrate (Thermo, 34580) was added and membranes were imaged on a Li-cor Odyssey imaging system.

Paraffin sections of formaldehyde-fixed pig kidney tissue were subjected to 1:1,000 human IgE mAb 16D9. After washing, secondary antibody (mouse anti-human IgE Fc; Southern biotech, 9160-05) was applied at a 1:1,000 dilution. Finally, immunoperoxidase staining was applied and low/high magnification images obtained to show extent and location of alpha-gal specific IgE mAb 16D9 binding.

Glycan microarray. A 600+ glycan microarray developed by the Consortium for Functional Glycomics was used to evaluate the epitope specificities of human IgE antibodies 16D9 and 10H8. The glycan microarray and alpha-gal specific analysis was performed at The Scripps Research Institute. Specific glycans which showed significant positivity in the large array were further studied individually for fine specificity comparisons with murine anti-alpha-gal antibody M86. As with other binding assays, the secondary antibody used in the microarray and specific alpha-gal binding assays was mouse anti-human IgE Fc from Southern biotech, in this case biotinylated, 9160-08. Alpha-gal control antibody M86 was purchased from Absolute antibody (Ab00532-14.0) as a recombinant human IgE mAb and was used as a comparator.

Variable gene sequencing of human alpha-gal specific IgE mAbs. Total RNA was extracted from 1 million clonal IgE-expressing human hybridoma cells (RNeasy kit, Qiagen: 74104). Reverse transcription PCR (RT-PCR) then was performed for 30 cycles with a 5' primer set described previously (Smith et al., 2009) and a 3' primer specific to the IgE constant using the OneStep RT-PCR kit (Qiagen: 210210). Following gel purification, the cDNA product was cloned into pCR2.1 using a TA cloning kit (Invitrogen: 45-0046). Antibody genes were Sanger sequenced and analyzed using the IMGT database, world-wide-web at imgt.org.

Example 2—Results

Identification of ultra-rare human alpha-gal specific IgE mAbs. Using red meat allergic patient serum IgE profiles and skin testing results, obtained by their allergist, the inventor was able to identify two subjects which not only had high titers of circulating IgE but also high frequencies (relatively speaking) of circulating IgE encoding B cells (see Table A). Cryopreserved PBMCs were thawed, grown in 96-well cultures, and screened for the IgE isotype to allow for identification of desired B cell clones. A secondary screen, by direct ELISA using the human therapeutic mAb cetuximab, was performed to allow for the identification of alpha-gal specific B cells in culture. Patient number 174 had a very high serum titers to alpha-gal, 86 kUA/L. An approximate minimum B cell frequency (#IgE expressing cultures/total #PBMCs cultured) can be calculated for each subject. Growth and screening of B cells from subject 174 revealed that their IgE encoding B cell frequency was 1.8 cells in 10 million peripheral blood mononuclear cells. Remarkably, secondary screening of the same B cell cultures revealed that subject 174 possessed alpha-gal specific IgE encoding B cells at a frequency of only 0.4 B cells per 10 million peripheral blood mononuclear cells, that is 4 cells in 100 million peripheral blood mononuclear cells. A total of nine human hybridomas secreting IgE antibody were obtained from subject 174, and four from subject 066. Finally, screening of purified IgE mAbs obtained from these subjects' hybridomas identified two from subject 174, 16D9 and 10H8, which were specific for the oligosaccharide gal-α1-3 gal using ImmunoCAP.

Verification and validation of IgE mAbs 16D9 and 10H8 alpha-gal specificity. Hybridoma supernatant was sent for conformational IgE testing against alpha-gal ImmunoCAP (o215, Thyroglobulin, bovine). Even when diluted 1:1,000, 10H8 supernatant measured 1,841 kUA/L and 16D9 measured 14,575 kUA/L, showing the impressive specificity and strength of binding of these human mAbs. After alpha-gal specificity was verified using Phadia ImmunoCAP, the inventor began molecular characterizations with assays to determine half maximal effective concentration ($EC_{50}$s) for binding to cetuximab and bovine thyroglobulin (BTG). By performing $EC_{50}$ assays using purified IgE mAb, rough comparisons between mAb binding can be made. As can be seen in FIG. 1A, binding is not identical between alpha-gal specific IgE mAbs. $EC_{50}$s for binding to cetuximab and BTG were determined using cetuximab: 16D9=20 ng/mL; 10H8=78 ng/mL and BTG: 16D9=16 ng/mL; 10H8=72 ng/mL. The relative binding affinities, as measured by approximate half maximal effective concentration, was obtained against cetuximab and BTG in a single ELISA plate to allow direct comparisons between human mAbs 16D9 & 10H8 and murine monoclonal antibody M86—shown in FIGS. 2A-B. The half maximal effective concentration of 16D9 is 10-fold lower than 10H8, showing that the affinity of 16D9 is significantly greater against alpha-gal present on both BTG and cetuximab. The half maximal effective concentration of 16D9 is around 100-fold, and 10H8 around 10-fold, lower than murine mAb M86. This shows that the affinity of both human IgE mAbs toward alpha-gal is significantly greater than the extensively studied alpha-gal specific murine mAb M86 (Absolute antibody, Ab00532-14.0).

Western blotting and immunohistochemistry was also performed using human mAbs 16D9 and 10H8—shown in FIGS. 1B-C. Immunoblotting patterns for cetuximab and BTG (10 g & 5 μg) under reducing and denaturing conditions are shown for 16D9 and 10H8 in FIG. 1B. As can be seen, only the heavy chain of cetuximab, which possesses the alpha gal containing glycan, is blotted by the human antibodies. Low and high magnification views of a porcine kidney, stained with IgE mAb 16D9 in immunohistochemistry, is shown in FIG. 1C. Strong staining is seen, focused on the kidney tubule cells, those cells known to possess high concentrations of glycans which contain alpha-gal.

Mapping the glycan binding profile of alpha-gal specific IgE mAbs 16D9 and 10H8. Alpha-gal is a very unique allergen, as it is not a protein. In its native form, alpha-gal is an disaccharide, making up a portion of a larger glycan, bound to a protein. How possessing IgE antibodies to a glycan can result in cross-linking of Fcε receptors is of foundational importance in understanding red meat allergy. The first step in understanding how this occurs is to map the fine epitope specificity of human IgE antibodies to red meat, 16D9 and 10H8. The fine specificity of glycan binding was determined for each of the human alpha-gal specific IgE mAbs in collaboration with The Scripps Research Institute. The inventor made use of the most advanced glycan mapping techniques available, employing a 600+ glycan microarray developed by the Consortium for Functional Glycomics.

The subtle nuances in their binding was elucidated using this glycan array technology. Shown in FIG. 3A is the total glycans for which each human mAb demonstrated binging on the microarray. These "hits" are further characterized in FIG. 3B. As can be seen, the heart of 10H8 and 16D9's epitope resides in the gal-α1-3 gal disaccharide. Both mAbs bind virtually identically to all glycans possessing the classical alpha-gal disaccharide unit. Very important differences, however, exist between these two human mAbs and murine mAb M86. The most important difference in the human and murine epitope relates to neighboring sugars. For example, both human mAbs are able to bind the alpha-gal disaccharide when the third sugar is attached by a β1-3 linkage. M86 is not able to bind these alpha-gal glycans, only binding glycans with β1-4 linkage attaching the third sugar. This very subtle difference can be seen in FIG. 3B, where the human antibodies can bind glycans labeled 103 (Galα1-3Galβ1-3GlcNAc) and 104 (Galα1-3Galβ1-4GlcNAc), while antibody M86 can only bind 104. In all cases, binding is entirely dependent on the glycan containing the terminal alpha-gal disaccharide gal-α1-3 gal somewhere in its structure. Additionally, significant improvement in human mAb binding occurs with biantennary alpha-gal structures. This is remarkable and shows that slight differences exist within a theorized mono-specific disease-causing antibody population. This suggests that there are more unique facets of specificity to alpha-gal binding antibodies than just binding the alpha-gal disaccharide, as the third sugar is clearly involved in the binding interface. This is a very important observation as it means that the only way to be certain that an alpha-gal containing antigen possesses the epitope needed to elicit the human B cell response in humans is by confirming it is bound by the antibodies of the human B cell response. In other words, to be certain that a given antigen is the allergen responsible for sensitizing humans, one must demonstrate binding by human IgE (not just murine antibody M86).

Variable gene sequence germline usage and mutation rate of human alpha-gal specific IgE mAbs. As can be seen in Table B, the sequences of these two human anti-alpha-gal IgE antibodies are unique, use different germline genes, have relatively short CDR3 sequences, and have a substantial number of mutations. Remarkably both human antibodies possess very high rates of mutations as compared to other antibodies previously described that target glycans, which are most frequently of the IgM isotype (Sterner et al., 2016). The total number of nucleotide mutations from their respective germline sequences for the heavy and light chains of 10H8 and 16D9 are 34 and 49 respectively. These unique IgE sequences will provide the allergen-specific reference needed to interrogate sequencing datasets and allow for further discovery of human antibodies to alpha-gal.

TABLE A

| IgE B-cell frequency and hybridoma yield | | | | | | | |
|---|---|---|---|---|---|---|---|
| Subject code | Disease | Total serum IgE (kU IgE/L) | Alpha-gal specific serum IgE (kUA/L) | Total PBMCs × $10^6$ | IgE B cell frequency (per $10^7$ PBMCs) | IgE hybridomas generated | Allergen specificity |
| 174 | DU | 1,063 | 86 | 204 | 1.8 | 23G2 | ND |
| | | | | | | 2D11 | ND |
| | | | | | | 16D9 | Alpha-gal |
| | | | | | | 5B8 | ND |
| | | | | | | 12E4 | ND |
| | | | | | | 5C10 | ND |
| | | | | | | 10H8 | Alpha-gal |
| | | | | | | 12H3 | ND |
| | | | | | | 9A12 | ND |
| 066 | DA | ND | 57 | 48 | 3.8 | 3C12 | ND |
| | | | | | | 17D1 | ND |
| | | | | | | 9D12 | ND |
| | | | | | | 1A13 | ND |

IgE B cell frequency is expressed as the number of IgE positive cells per 10 million peripheral blood mononuclear cells.
DA = delayed anaphylaxis;
DU = delayed urticaria;
ND = not determined.

TABLE B

| Genetic features of alpha-gal-specific human IgE mAbs | | | | | | | | | | | | |
|---|---|---|---|---|---|---|---|---|---|---|---|---|
| | Light | Germline Gene Segments | | | | | | CDR3 | Variable Gene Mutations | | | |
| IgE MAb | Chain | VH | D | JH | VL | JL | AA Junction | Length | VH NT | VH AA | VL NT | VLAA |
| 10H8 | κ | 3-33 | 15-1 | 6 | 2-30 | 2 | CARESEEQGNMDVW | 12 | 17 | 8 | 17 | 10 |
| 16D9 | λ | 4-34 | 1-1 | 4 | 2-14 | 1 | CGRGRGYTWNDW | 10 | 24 | 15 | 25 | 15 |

Ab germline gene segment usages are shown for variable (V), diverse (D), and joining (J) regions of both light and heavy chains based on ImMunoGeneTics, IMGT database. The number of nucleotide and amino acid mutations are shown.

TABLE 1

| NUCLEOTIDE SEQUENCES FOR ANTIBODY VARIABLE REGIONS | | | |
|---|---|---|---|
| Clone | SEQ ID NO: | Chain | Variable Sequence Region |
| 16D9 | 1 | heavy | CAGGTGCAGCTACAACAGTGGGGCGCAGGACTGTTGAAGCCATCGGAGACCCTGTCCCTCAC<br>CTGCGCTGTCTATGGTGGGACGTTCAGTGATTACTTCTATACCTGGATCCGCCAGCCCCCAG<br>GGAAGGGGCTGGAGTGGATTGGGGAAGTCAGTCATACTGGGAGGACCAGCTACATCCCGTCC<br>CTCAAGAGTCGAGTCACCATGTCAGTAGACACGTCTAAAAACCAGTTCTCCCTGAACTTGAG<br>CTCTGTGACCGACGCGGACACGGCTGTTTATTATTGTGGGAGAGGTCGGGGTTACACTTGGA<br>ATGATTGGGGCCAGGGAACGCTAGTCACCGTCTCCTCAG |
| | 2 | light | CAGTCTGCCCTGACTCAGCCTGCCTCCGTGTCTGGGTCTCCTGGACAGTCGATCACCATCTC<br>CTGCACTGGAACCATCACTGACGTTGGTGGTTATGACTATGTCTCCTGGTACCAACAACACC<br>CAGGCAAAGCCCCCAAACTCATCATTTTCCTTGTCAATAATCGGCCCTCAGGGGTTTCTGAT<br>CGCTTCTCTGGCTCCAAGTCTGGCAACACGGCCTCCCTGACCATCTCAGGGCTCCGGGTTGA<br>GGACGAGGCTGATTATTATTGCATGTCATATACATGCAGCAACCCATATACATGCAGCAGCC<br>TTTATGTCTTCGGAACTGGGACCAAGGTCACCGTCCTGG |
| 10H8 | 3 | heavy | CAGGTGCAGCTGGTGGAGTCGGGGGGAGGCGTGGTCCAGCCTGGGAGGTCCCTGAGACTCTC<br>CTGTGCGGTGTCTGGATTCACCTTCAGGAGCTTTGGCATGCACTGGGTCCGCCAGGCTCCGG<br>GCAAGGGGCTGGAGTGGGTGGCAGTCATATGGCATGATGGAAGTAACAAGCACTATGCAGAC<br>TCCGTGAAGGGCCGATTCACCATTTCCAGAGACGACTCCAAGAACACCCTGTTTCTGCAAAT<br>GAACAGCCTGAGAGCCGAGGACACGGCTGTGTATTATTGTGCGAGAGAATCGGAGGAACAGG<br>GAAATATGGACGTCTGGGGCCAAGGGACCACGGTCACCGTCTCCTCA |
| | 4 | light | GATGTTGTGATGACTCAGTCTCCACTCTCCCTGCCCGCCACCCTTGGCCAGCCGGCCTCCAT<br>CTCCTGCAGGTCTAGTCATAGCCTCGTTTACAGTAATGGAAACACCTACTTGAATTGGTTTC<br>AGCAGAGGCCAGGCCAATCTCCAAGGCGCCTGTTTTTTCAGGTTTCTAACCGGGACTCTGGG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | GTCCCAGACAGATTCAGCGGCAGTGGGTCCGTAACTAATTTCACACTGAAAATCAGCAGGGT GGAGGCTGAGGATGTTGGGGTCTACTACTGCATGGAAGGTTCACACTGGCCTCCGTACACTT TTGGCCAGGGGACCAGGCTGGACATCAGAC |

TABLE 2

PROTEIN SEQUENCES FOR ANTIBODY VARIABLE REGIONS

| Clone | SEQ ID NO: | Chain | Variable Sequence |
|---|---|---|---|
| 16D9 | 5 | heavy | QVQLQQWGAGLLKPSETLSLTCAVYGGTFSDYF YTWIRQPPGKGLEWIGEVSHTGRTSYIPSLKSR VTMSVDTSKNQFSLNLSSVTDADTAVYYCGRGR GYTWNDWGQGTLVTVSS |
| | 6 | light | QSALTQPASVSGSPGQSITISCTGTITDVGGYD YVSWYQQHPGKAPKLIIFLVNNRPSGVSDRFSG SKSGNTASLTISGLRVEDEADYYCMSYTCSNPY TCSSLYVFGTGTKVTVL |
| 10H8 | 7 | heavy | QVQLVESGGGVVQPGRSLRLSCAVSGFTFRSFG MHWVRQAPGKGLEWVAVIWHDGSNKHYADSVKG RFTISRDDSKNTLFLQMNSLRAEDTAVYYCARE SEEQGNMDVWGQGTTVTVSS |
| | 8 | light | DVVMTQSPLSLPATLGQPASISCRSSHSLVYSN GNTYLNWFQQRPGQSPRRLFFQVSNRDSGVPDR FSGSGSVTNFTLKISRVEAEDVGVYYCMEGSHW PPYTFGQGTRLDIR |

TABLE 3

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| 16D9 | GGTFSDYF (9) | VSHTGRT (10) | GRGRGYTWND (11) |
| 10H8 | GFTFRSFG (12) | IWHDGSNK (13) | ARESEEQGNMDV (14) |

TABLE 4

CDR LIGHT CHAIN SEQUENCES

| Clone | CDRL1 (SEQ ID NO:) | CDRL2 | CDRL3 (SEQ ID NO:) |
|---|---|---|---|
| 16D9 | ITDVGGYDY (15) | LVN | MSYTCSNPYTCSSLYV (16) |
| 10H8 | HSLVYSNGNTY (17) | QVS | MEGSHWPPYT (18) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, N Y, 1988.
Abbondanzo et al., *Am. J. Pediatr. Hematol. Oncol.* 12(4): 480-489, 1990.
Allred et al., *Arch. Surg.* 125(1), 107-113: 1990.
Atherton et al., *Biol. of Reproduction* 32: 155-171, 1985.
Barzon et al., *Euro Surveill.* 11: 21(32), 2016.
Beltramello et al., *Cell Host Microbe* 8: 271-283, 2010.
Brown et al., *J. Immunol. Meth.* 130(1): 111-121, 1990.
Campbell, *In: Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.* 74(2):4 25-433, 1977.
De Jager et al., *Semin. Nucl. Med.* 23(2): 165-179, 1993.
Dholakia et al., *J. Biol. Chem.* 264: 20638-20642, 1989.
Diamond et al., *J. Virol.* 77: 2578-2586, 2003.
Doolittle and Ben-Zeev, *Methods Mol. Biol.* 109: 215-237, 1999.
Duffy et al., *N. Engl. J. Med.* 360: 2536-2543, 2009.

Elder et al. Infections, infertility and assisted reproduction. Part II: Infections in reproductive medicine & Part III: Infections and the assisted reproductive laboratory. Cambridge UK: Cambridge University Press; 2005.
Gefter et al., *Somatic Cell Genet.* 3: 231-236, 1977.
Gornet et al., *Semin Reprod Med.* 34(5): 285-292, 2016.
Gulbis and Galand, *Hum. Pathol.* 24(12): 1271-1285, 1993.
Halfon et al., *PLoS ONE* 5(5): e10569, 2010
Hessell et al., *Nature* 449: 101-104, 2007.
Khatoon et al., *Ann. of Neurology* 26: 210-219, 1989.
King et al., *J. Biol. Chem.* 269: 10210-10218, 1989.
Kohler and Milstein, *Eur. J. Immunol.* 6: 511-519, 1976.
Kohler and Milstein, *Nature* 256: 495-497, 1975.
Kyte and Doolittle, *J. Mol. Biol.* 157(1): 105-132, 1982.
Mansuy et al., *Lancet Infect Dis.* 16(10): 1106-7, 2016.
Nakamura et al., In: *Enzyme Immunoassays: Heterogeneous and Homogeneous Systems*, Chapter 27, 1987.
O'Shannessy et al., *J. Immun. Meth.* 99: 153-161, 1987.
Persic et al., *Gene* 187: 1, 1997
Potter and Haley, *Meth. Enzymol.* 91: 613-633, 1983.
Purpura et al., *Lancet Infect Dis.* 16(10): 1107-8, 2016.
Remington's Pharmaceutical Sciences, 15th Ed., 3: 624-652, 1990.
Smith et al., *Nat Protoc.* 2009; 4(3):372-384.
Sterner et al., *ACS Chem Biol.* 2016; 11(7):1773-1783.
Tang et al., *J. Biol. Chem.*, 271: 28324-28330, 1996.
Wawrzynczak & Thorpe, In: *Immunoconjugates, Antibody Conjugates In Radioimaging And Therapy Of Cancer*, Vogel (Ed.), NY, Oxford University Press, 28, 1987.
Wurth et al., *JCI Insight.* 2018; 3(20):e123387.
Yu et al., *J Immunol Methods* 336: 142-151, 2008.

What is claimed is:

1. A method of detecting galactose-α-1,3-galactose (alpha-gal) in a sample comprising:

(a) contacting a sample with an antibody or antibody fragment comprising (i) heavy chain CDR1-3 comprising SEQ ID NOS: 9, 10 and 11, respectively, and light chain CDR1-3 comprising SEQ ID NOS: 15, 16 and 17, respectively, or (ii) heavy chain CDR1-3 comprising SEQ ID NOS: 12, 13 and 14, respectively, and light chain CDR1-3 comprising SEQ ID NOS: 18, 19 and 20, respectively; and (b) detecting alpha-gal in said sample by binding of said antibody or antibody fragment to alpha-gal in said sample.

2. A method of detecting IgE anti-galactose-α-1,3-galactose (alpha-gal) antibodies in a sample comprising:

(a) contacting a sample suspected IgE anti-alpha gal antibodies with alpha-gal in a competitive assay with an antibody or antibody fragment comprising (i) heavy chain CDR1-3 comprising SEQ ID NOS: 9, 10 and 11, respectively, and light chain CDR1-3 comprising SEQ ID NOS: 15, 16 and 17, respectively, or (ii) heavy chain CDR1-3 comprising SEQ ID NOS: 12, 13 and 14, respectively, and light chain CDR1-3 comprising SEQ ID NOS: 18, 19 and 20, respectively; and (b) detecting competition for binding of alpha-gal by a suspected IgE anti-alpha gal in said sample by an antibody or antibody fragment comprising (i) heavy chain CDR1-3 comprising SEQ ID NOS: 9, 10 and 11, respectively, and light chain CDR1-3 comprising SEQ ID NOS: 15, 16 and 17, respectively, or (ii) heavy chain CDR1-3 comprising SEQ ID NOS: 12, 13 and 14, respectively, and light chain CDR1-3 comprising SEQ ID NOS: 18, 19 and 20, respectively.

3. A method of preventing or treating an alpha-gal-related allergic reaction in a subject comprising delivering to said subject an IgG antibody or antibody fragment comprising (i) heavy chain CDR1-3 comprising SEQ ID NOS: 9, 10 and 11, respectively, and light chain CDR1-3 comprising SEQ ID NOS: 15, 16 and 17, respectively, or (ii) heavy chain CDR1-3 comprising SEQ ID NOS: 12, 13 and 14, respectively, and light chain CDR1-3 comprising SEQ ID NOS: 18, 19 and 20, respectively.

4. An IgG monoclonal antibody or antibody fragment thereof, wherein the antibody or antibody fragment comprises (i) heavy chain CDR1-3 comprising SEQ ID NOS: 9, 10, and 11, respectively, and light chain CDR1-3 comprising SEQ ID NOS: 15, 16 and 17, respectively, or (ii) heavy chain CDR1-3 comprising SEQ ID NOS: 12, 13 and 14, respectively, and light chain CDR1-3 comprising SEQ ID NOS: 18, 19 and 20, respectively.

5. The IgG monoclonal antibody or antibody fragment of claim 4, wherein said antibody or antibody fragment is encoded by heavy and light chain variable regions comprising SEQ ID NOS: 1 and 2, respectively, or SEQ ID NOS: 3 and 4, respectively.

6. The IgG monoclonal antibody or antibody fragment of claim 4, wherein said antibody or antibody fragment is encoded by heavy and light chain variable regions having at least 80%, 90%, or 95% identity to SEQ ID NOS: 1 and 2, respectively, or SEQ ID NOS: 3 and 4, respectively.

7. The IgG monoclonal antibody or antibody fragment of claim 4, wherein said antibody or antibody fragment comprises heavy and light chain variable sequences comprising SEQ ID NOS: 5 and 6, respectively, or SEQ ID NOS: 7 and 8, respectively.

8. The IgG monoclonal antibody or antibody fragment of claim 4, wherein said antibody or antibody fragment comprises heavy and light chain variable regions having 95% identity to SEQ ID NOS: 5 and 6, respectively, or SEQ ID NOS: 7 and 8, respectively.

9. The IgG monoclonal antibody or antibody fragment of claim 4, wherein the antibody fragment is a recombinant scFv (single chain fragment variable) antibody, Fab fragment, $F(ab')_2$ fragment, or Fv fragment.

10. The IgG monoclonal antibody or antibody fragment of claim 4, wherein said antibody is a chimeric antibody or bispecific antibody.

11. The IgG monoclonal antibody or antibody fragment of claim 4, wherein said antibody comprises an Fc portion mutated to alter FcR interactions, to increase half-life and/or increase therapeutic efficacy, or glycan modified to alter FcR interactions.

12. The monoclonal antibody or antibody fragment of claim 11, wherein the Fc portion mutated to alter FcR interactions, to increase half-life and/or increase therapeutic efficacy is selected from the group consisting of a LALA mutation, a LALA-PG mutation, an N297 mutation, a GASD/ALIE mutation, a DHS mutation, a YTE mutation or a LS mutation, and wherein the glycan modification to alter FcR interactions is enzymatic or chemical addition or removal of glycans or expression in a cell line engineered with a defined glycosylating pattern.

13. The IgG monoclonal antibody or antibody fragment of claim 4, wherein said antibody or antibody fragment further comprises a cell penetrating peptide and/or is an intrabody.

14. An engineered cell encoding an antibody or antibody fragment wherein the antibody or antibody fragment comprises (i) heavy chain CDR1-3 comprising SEQ ID NOS: 9, 10 and 11, respectively, and light chain CDR1-3 comprising SEQ ID NOS: 15, 16 and 17, respectively, or (ii) heavy chain CDR1-3 comprising SEQ ID NOS: 12, 13 and 14, respectively, and light chain CDR1-3 comprising SEQ ID NOS: 18, 19 and 20, respectively.

15. The engineered cell of claim 14, wherein said antibody or antibody fragment is encoded by heavy and light chain variable regions comprising SEQ ID NOS: 1 and 2, respectively, or SEQ ID NOS: 3 and 4, respectively.

16. The engineered cell of claim 14, wherein said antibody or antibody fragment is encoded by heavy and light chain variable regions having at least 80%, 90%, or 95% identity to SEQ ID NOS: 1 and 2, respectively, or SEQ ID NOS: 3 and 4, respectively.

17. The engineered cell of claim 14, wherein said antibody or antibody fragment comprises heavy and light chain variable regions comprising SEQ ID NOS: 5 and 6, respectively, or SEQ ID NOS: 7 and 8, respectively.

18. The engineered cell of claim 14, wherein said antibody or antibody fragment comprises heavy and light chain variable regions having at least 95% identity to variable regions comprising SEQ ID NOS: 5 and 6, respectively, or SEQ ID NOS: 7 and 8, respectively.

19. The hybridoma or engineered cell of claim 14, wherein the antibody fragment is a recombinant scFv (single chain fragment variable) antibody, Fab fragment, $F(ab')_2$ fragment, or Fv fragment.

20. The hybridoma or engineered cell of claim 14, wherein said antibody is a chimeric or bispecific antibody.

21. A method of de-sensitizing a subject to galactose-α-1,3-galactose (alpha-gal) comprising:

(a) administering to said subject galactose-α-1,3-galactose (alpha-gal); and (b) administering to said subject an IgG antibody that has a binding specificity to galactose-α-1,3-galactose (alpha-gal) fragment and comprising (i) heavy chain CDR1-3 comprising SEQ ID NOS: 9, 10 and 11, respectively, and light chain CDR1-3 comprising SEQ ID NOS: 15, 16 and 17, respectively, or (ii) heavy chain CDR1-3 comprising SEQ ID NOS: 12, 13 and 14, respectively, and light chain CDR1-3 comprising SEQ ID NOS: 18, 19 and 20, respectively.

22. A monoclonal antibody or antibody fragment thereof comprising (i) heavy chain CDR1-3 comprising SEQ ID NOS: 9, 10, and 11, respectively, and light chain CDR1-3 comprising SEQ ID NOS: 15, 16 and 17, respectively, or (ii) heavy chain CDR1-3 comprising SEQ ID NOS: 12, 13 and 14, respectively, and light chain CDR1-3 comprising SEQ ID NOS: 18, 19 and 20, respectively, wherein the antibody or antibody fragment comprises an Fc portion mutated to alter FcR interactions, to increase half-life and/or increase therapeutic efficacy or is glycan modified to alter FcR interactions.

23. The monoclonal antibody or antibody fragment of claim 22, wherein the Fc portion mutated to alter FcR interactions, to increase half-life and/or increase therapeutic efficacy is selected from the group consisting of a LALA mutation, a LALA-PG mutation, an N297 mutation, a GASD/ALIE mutation, a DHS mutation, a YTE mutation or a LS mutation, and wherein the glycan modification to alter FcR interactions is enzymatic or chemical addition or removal of glycans or expression in a cell line engineered with a defined glycosylating pattern.

* * * * *